United States Patent [19]

Tsubai et al.

[11] Patent Number: 5,888,526
[45] Date of Patent: Mar. 30, 1999

[54] ANTIBACTERIAL ANTIFUNGAL AGENT AND FIBROUS MATERIAL CONTAINING THE SAME

[75] Inventors: Yasuo Tsubai; Mitsuo Yoshida; Eisuke Yamaya, all of Tokyo, Japan

[73] Assignee: Mitsubishi Paper Mills Limited, Tokyo, Japan

[21] Appl. No.: 828,811

[22] Filed: Apr. 3, 1997

[30] Foreign Application Priority Data

| | | | |
|---|---|---|---|
| Apr. 5, 1996 | [JP] | Japan | 8-083469 |
| Apr. 12, 1996 | [JP] | Japan | 8-091154 |
| Feb. 28, 1997 | [JP] | Japan | 9-045930 |

[51] Int. Cl.⁶ ............................................. A01N 25/10
[52] U.S. Cl. .................. 424/405; 424/402; 424/404; 424/406; 424/409; 424/411; 424/417; 424/418; 424/419; 424/421; 424/618; 424/630; 424/631; 424/641; 424/78.1; 424/78.13; 424/78.14; 424/78.15
[58] Field of Search ................... 424/404, 402, 424/406, 409, 411–415, 417–419, 421, 618, 630, 631, 641, 78.09, 78.1, 78.13–78.15, 76.8

[56] References Cited

U.S. PATENT DOCUMENTS

| | | | |
|---|---|---|---|
| 2,809,971 | 10/1957 | Bernstein et al. | 260/270 |
| 4,565,856 | 1/1986 | Trotz et al. | 526/265 |
| 5,496,860 | 3/1996 | Matsumoto et al. | 521/31 |
| 5,516,519 | 5/1996 | Oka et al. | 424/405 |
| 5,541,233 | 7/1996 | Roenigk | 521/54 |
| 5,561,167 | 10/1996 | Matsumoto et al. | 521/31 |
| 5,595,750 | 1/1997 | Jacobson et al. | 424/421 |

FOREIGN PATENT DOCUMENTS

| | | |
|---|---|---|
| 0 149 175 | 12/1984 | European Pat. Off. . |
| 0 727 427 | 10/1994 | European Pat. Off. . |
| 55-62906 | 11/1978 | Japan . |
| 55-122556 | 3/1979 | Japan . |
| 63-270900 | 4/1987 | Japan . |
| 2-288804 | 6/1989 | Japan . |
| 3-113076 | 9/1989 | Japan . |
| 4-126819 | 9/1990 | Japan . |
| 5-106199 | 10/1991 | Japan . |
| 5-7617 | 10/1991 | Japan . |
| 5-214671 | 2/1992 | Japan . |
| 6-200472 | 12/1992 | Japan . |
| 6-256689 | 12/1992 | Japan . |
| 6-256755 | 12/1992 | Japan . |
| 7-126432 | 11/1993 | Japan . |
| 7-133444 | 11/1993 | Japan . |
| 8-176961 | 12/1994 | Japan . |

OTHER PUBLICATIONS

Derwent Publications Ltd., Database WPI, Section Ch, Week 9145, London, GB; Class A23, AN 91–329304, XP002065243 & JP 03 220 307 A (Unitika Ltd), 27 Sep. 1991.

Derwent Publications Ltd., Database WPI, Section Ch, Week 9140, London, GB; Class D22, AN 91–291702, XP002065245 & JP 03 193 707 A (Toyo Dry Roove KK), 23 Aug. 1991.

Derwent Publications Ltd., Database WPI, Section Ch, Week 8948, London, GB; Class A88, AN 89–352147, XP002065246 & JP 01 262 989 A (Matsushita Elec Ind Co Ltd), 19 Oct. 1988.

Derwent Publications Ltd., Database WPI, Section Ch, Week 9443, London, GB; Class A60, AN 94–347648, XP002065244 & JP 06 272 173 A (Teijin Ltd), 27 Sep. 1994.

*Primary Examiner*—Neil S. Levy
*Attorney, Agent, or Firm*—Pillsbury Madison & Sutro LLP

[57] ABSTRACT

The present invention is to provide a fibrous material containing an antibacterial antifungal agent consisting of specific metal salt of organic compound effective for both antibacterial and antifungal functions and various articles containing the same fibrous material. The inclusion of the antibacterial antifungal agent consisting of specific metal salt of organic compound in fibrous materials allows production of fibrous materials having extremely high antibacterial antifungal activity. Various articles containing the fibrous materials have found to exhibit excellent antibacterial antifungal effects.

22 Claims, No Drawings

ANTIBACTERIAL ANTIFUNGAL AGENT AND FIBROUS MATERIAL CONTAINING THE SAME

BACKGROUND OF THE INVENTION

The present invention relates to an antibacterial antifungal agent and a fibrous material containing the same. More particularly, it relates to an antibacterial antifungal agent that is extremely effective as both bactericide and antimold, well functional to a contamination at a high fungal concentration, highly durable, and significantly resistant to a reduction in effectiveness and in release contamination due to washing, and highly safe, and it relates to a fibrous material containing the same. Moreover, the present invention relates to various things having fibrous materials containing the antibacterial antifungal agents, for example, air filters of room cleaning conditioners used in the facilities of semiconductor manufacturing industries, pharmaceutical industries, food industries, hospitals and the like, filters for office and domestic room conditioners. Particularly, it relates to filters having antibacterial antifungal functions which may be applied to air filters used in various vehicles, such as automobiles. Still more particularly, the present invention relates to a wide variety of articles, especially various filter materials which are extremely effective as both bactericide and antimold, well functional to a contamination at a high fungal concentration, highly durable, and significantly resistant to a reduction in effectiveness and in release contamination due to washing, and highly safe.

Recently there have been marketed a wide variety of fibrous products having antibacterial and antifungal functions in response to an ever increasing user's requirement of rendering equipments more and more sanitary. It has been well known heretofore that inorganic compounds such as metal salts of silver, copper, zinc and the like have an antibacterial property. It has also been well known that organic compounds such as pyrrole, pyridine, pyrimidine, imidazole, and thiazole compounds have an antifungal property.

There is generally a great tendency, however, that inorganic metal salts are inferior in an antimold effect though they have an antibacterial effect, while organic compounds are inferior in an antibacterial effect though they have an antifungal effect. There has been no material which has both sufficient antibacterial and antifungal functions.

Recently, as a matter of fact, manufacturers have directed a great effort in coping with the increasing need for various fibrous articles which have both antibacterial and antifungal functions.

Many attempts have been made heretofore to apply various inorganic metal salt compounds and organic compounds as described above to various products for the purpose of imparting the antibacterial and antifungal functions.

Japanese Patent KOKAI (Laid-open) No. Hei 7-126432 discloses an antibacterial antifungal resin composition comprising resin having a complex of an Ag ion coordinated by thiol-containing compounds.

Japanese Patent KOKAI No. Hei 7-133444 discloses an antibacterial paint composition comprising an antibacterial agent and a vehicle where the antibacterial agent is a metal complex having an Ag, Co, Zn, Sn or Cr ion coordinated by coordination compounds which have an alkoxysilyl group and a coordination group coordinatable with the metal ions in the molecule.

Japanese Patent KOKAI No. Hei 5-7617 discloses a deodorant material having acidic groups which contains a specific gram equivalent per gram polymer of acidic groups which are substituted with at least one metal ion selected from the group consisting of Zn, Cu, Ni, Mn, Ag and Fe ions.

Japanese Patent KOKAI No. Hei 5-214671 discloses a deodorizing antibacterial fibers consisting of ion-exchange fibers, at least a part of which are substituted with metal ions having an antibacterial activity and with ions having a deodorizing activity.

Japanese Patent KOKAI No. Hei 6-200472 discloses antibacterial fibers comprising ion-exchange fibers and metal ions having an antibacterial activity trapped in the ion-exchange fibers by ion-exchange reaction.

Japanese Patent KOKAI No. Sho 63-270900 discloses cellulose fibers which have a deodorizing ability and a formability into paper comprising carboxymethylated cellulose fibers at a carboxymethyl substitution degree of 0.35 or less having Cu ions and/or Zn ions absorbed on the fibers.

Japanese Patent KOKAI No. Hei 5-106199 discloses an antibacterial fibers which are produced by depositing inorganic silicon compounds within fibers, then immersing the inorganic silicon compound bearing fibers in a solution of an alminate salt and thereafter treating the fibers by immersing in a solution containing at least one selected from the group consisting of water soluble salts of copper, silver and zinc.

Japanese Patent KOKAI No. Hei 6-248549 discloses a non-woven fabric comprising substantially water insoluble pulp fibers containing an antibacterial agent, said fiber sheet being insoluble in water or of a low solubility, which is produced by stratifying fiber sheets on the surface of a long fiber non-woven fabric having a number of long fibers stratified, and passing a columnar flow of water under a high pressure through the laminate from the side of said sheets to the opposite side of the said long fiber non-woven fabric, whereby the fibers forming said sheets are cross-linked with the long fibers forming said long fiber non-woven fabric.

Japanese Patent KOKAI No. Hei 4-126819 discloses polyvinyl alcohol fibers having an antibacterial activity which contain 2-(4-thiazolyl)-benzimidazole or 2-(carbomethoxyamino)-benzimidazole.

However, none of those methods is capable of providing a material having sufficiently both antibacterial and antifungal functions, and particularly there still remains a problem of durability.

Antibacterial agents such as organic compounds of heavy metal salts have been known for a long time as, for example, U.S. Pat. No. 2,809,971 discloses heavy metal salts of 1-hydroxy-2-pyridinethion. It claims zinc salts, manganese salts, iron salts, cobalt salts and copper salts as the heavy metal salts.

As further described in U.S. Pat. No. 2,809,971, the organic compounds of heavy metal salts are used in leather, paper, paints, and particularly applicable to plastics and fabrics by impregnation and spray processing.

Said U.S. Patent describes that the fabrics are treated with pyridinethiol followed by treating with water soluble heavy metal salts.

In this method, however, initial effects may be obtained, but released contamination and deterioration due to washing, friction and the like may happen. Thus, the products are likely to be devoid of sustained effects.

Recently a variety of articles including various fibrous products, especially filter materials, having antibacterial and antifungal functions have been marketed on the background of an increasing user's requirement for more sanitary.

Many attempts have been made heretofore to apply antibacterial antifungal agents, particularly various fibrous materials containing inorganic metal salt compounds to, for example, filter materials for the purpose of imparting the antibacterial and antifungal functions.

Japanese Patent KOKAI No. Hei 6-285314 discloses a non-woven fabric provided as antibacterial filter sheet which is produced by mixing Ag containing glass fibers having a specific average diameter and containing monovalent Ag ions with Ag free glass fibers having a specific average diameter and a specific average length, and making the mixture into paper.

Japanese Patent KOKAI No. Hei 6-285314 discloses a deodorizing antibacterial filter sheet comprising a non-woven fabric which is produced by paper-making the mixture of activated carbon filters and Ag containing glass fibers which contain monovalent Ag ions.

Japanese Patent KOKAI No. Hei 6-269619 discloses an antibacterial hotmelt sheet characterized in that breathable sheets are bonded to each other with a breathable antibacterial hotmelt sheets so as to be breathable throughout all the sheets.

Japanese Patent KOKAI No. Hei 7-108120 discloses a process for producing an antibacterial air filter characterized in that a metal fume having an antibacterial activity is entrained in an air flow passing through between filter fibers which the filter is made of so that the metal fume is deposited on the filter fibers when the metal fume containing air passes through the air filter.

However, none of the methods as above can provide articles including various fibrous materials having both antibacterial and antifungal functions, and especially none of prior filter materials has sufficient antibacterial and antifungal functions, and particularly there still remains a problem of durability.

SUMMARY OF THE INVENTION

The present inventors have made an intensive research in view of the current situation as above. As a result, they have found an antibacterial antifungal agent which is extremely effective to inhibit both bacteria and mold and has various excellent characteristics and also have found that fibrous materials containing said antibacterial antifungal agent exhibits extremely outstanding effects. The present invention has been completed based on this discovery.

That is, an object of the present invention is to provide an antibacterial antifungal agent which is extremely effective to inhibit both bacteria and mold, and to provide a fibrous material containing said antibacterial antifungal agent which is stable over an extended period of time, non-releasable even with washing, extremely effective to a high concentration of bacteria contaminants.

Moreover, the present invention enables the provision of a filter material having extremely excellent antibacterial and antifungal functions, i.e., having both sufficient antibacterial and antifungal functions without impairing filter performance by applying the fibrous material containing the antibacterial antifungal agent comprising an organic metal salt compound (which is sometimes referred to as fibrous material of the present invention hereinunder) to various articles, especially filter materials.

Antibacterial antifungal agents according to the present invention comprises specific metal salts of organic compounds which themselves have basically an antifungal property. Fibrous materials having excellent antibacterial and antifungal functions according to the present invention are produced by forming fibers containing the metal salts of organic compounds.

The organic compounds may be selected from compounds containing at least one of sulfur atom and heterocyclic rings with hetero-nitrogen atom. The organic compounds include those having as basic frame, for example, pyrrole, pyridine, pyrimidine, pyrazole, imidazole, benzinidazole, 1,3,5,-triazine, hexahydro-1,3,5-triazine, triazole, iso-oxazole, thiazole, benzothiazole, thiazolone, benzothiazolone, isothiazolone, benzoisothiazolone, tetrahydro-thiadiazinethion, and in addition, alkylaryl derivatives and mercapto derivatives thereof. Specifically preferred among them are at least one selected from benzimidazole compounds, mercaptopyridine-N-oxide compounds, isothiazolone compounds, benzothiazole compounds and benzothiazolone compounds.

Practical examples include, for example, 2-(4-thiazolyl) benzimidazole, 2-(carbomethoxyamino)-benzimidazole, 2-mercaptopyridine-N-oxide, 1,2,-benzisotriazoline-3-one, 5-chloro-2-methyl-4-isotriazoline-3-one, 2-methyl-4-isothiazoline-3-one, 2-n-octyl-4-isothiazoline-3-one, 1,2-benzothiazolone, 2-(4-thiocyanomethylthio)benzothiazole and the like.

These metal salts may be selected from silver salts, copper salts and zinc salts. Preferably the metal salts are complex salts of metal salts of two or more of silver, copper and zinc, most preferably complex salts of metal salts of three of silver, copper and zinc.

More particularly, as a result of an intensive research to overcome the difficulties as described above, the following embodiments have been achieved:

1. The present invention is a fibrous material containing an antibacterial antifungal agent comprising a metal salt of an organic compound.
2. A fibrous material according to the above embodiment 1, wherein said fibrous material is ion-exchange fibers.
3. A fibrous material according to the above embodiment 1, wherein said organic compound is a compound containing at least one of sulfur atoms and heterocyclic rings with hetero-nitrogen atom.
4. A fibers material according to the above embodiment 3, wherein said organic compound containing at least one of sulfur atoms and heterocyclic rings with hetero-nitrogen atom is at least one selected from the group consisting of benzimidazole compounds, mercaptopyridine-N-oxide compounds, isothiazolone compounds, benzothiazole compounds and benzothiazolone compounds.
5. A fibrous material according to the above embodiment 1, wherein said metal salt is at least one selected from silver salts, copper salts and zinc salts.
6. A fibrous material according to the above embodiment 5, wherein said metal salt is a complex of two or more of a silver salt, a copper salt and a zinc salt.
7. A fibrous material according to the above embodiment 6, wherein said metal salt is a complex of three of a silver salt, a copper salt and a zinc salt.
8. A fibrous material according to the above embodiment 7, wherein said complex of three of a silver salt, a copper salt and a zinc salt has a composition of 10 to 40 silver, 20 to 60 zinc and the remainder copper by mole based on 100 moles of the total of metals, provided that the amount of copper is never zero.
9. A fibrous material according to the above embodiment 2, wherein said ion-exchange fibers are of at least one selected from polystyrenes, polyacrylics, polyamides, polyesters, polyethylenes and cellulose and having at least one of sulfonic acid group, phosphonic acid group and carboxylic acid group.

10. A fibrous material according to the above embodiment 9, wherein said ion-exchange fibers are carboxymethyl-modified fibers.

11. A fibrous material according to the above embodiment 10, wherein said ion-exchange fibers are carboxymethyl-modified cellulose fibers.

12. A fibrous material according to the above embodiment 11, wherein said carboxymethyl-modified cellulose fibers have a degree of modification as measured by a degree of substitution of 0.5 or less.

13. A fibrous material according to the above embodiment 11, wherein a proportion of said antibacterial antifungal agent is 1% or more solids by weight based on said carboxymethyl-modified cellulose fibers.

14. A fibrous material containing an antibacterial antifungal agent produced by adding a metal salt of to ion-exchange fibers and then adding an organic compound.

15. A fibrous material containing an antibacterial antifungal agent according to the above embodiment 14, wherein said metal salt is at least one selected from silver salts, copper salts and zinc salts.

16. A fibrous material containing an antibacterial antifungal agent according to the above embodiment 15, wherein said metal salt is a complex of two or more of a silver salt, a copper salt and a zinc salt.

17. A fibrous material containing an antibacterial antifungal agent according to the above embodiment 16, wherein said metal salt is a complex of three of a silver salt, a copper salt and a zinc salt.

18. A fibrous material containing an antibacterial antifungal agent according to the above embodiment 14, wherein said organic compound is a compound containing at least one of sulfur atoms and heterocyclic rings with hetero-nitrogen atom.

19. A fibrous material containing an antibacterial antifungal agent according to the above embodiment 18, wherein said organic compound containing at least one of sulfur atoms and heterocyclic rings with hetero-nitrogen atom is at least one selected from the group consisting of benzimidazole compounds, mercaptopyridine-N-oxide compounds, isothiazolone compounds, benzothiazole compounds and benzothiazolone compounds.

20. A fibrous material containing an antibacterial antifungal agent according to the above embodiment 14, wherein said ion-exchange fibers are of at least one selected from polystyrenes, polyacrylics, polyamides, polyesters, polyethylenes and cellulose and having at least one of sulfonic acid group, phosphonic acid group and carboxylic acid group.

21. A fibrous material containing an antibacterial antifungal agent according to the above embodiment 20, wherein said ion-exchange fibers are carboxymethyl-modified fibers.

22. A fibrous material containing an antibacterial antifungal agent according to the above embodiment 21, wherein said ion-exchange fibers are carboxymethyl-modified cellulose fibers.

23. A fibrous material containing an antibacterial antifungal agent according to the above embodiment 22, wherein said carboxymethyl-modified cellulose fibers have a degree of modification as measured by a degree of substitution of 0.5 or less.

24. A fibers material containing an antibacterial antifungal agent according to the above embodiment 14, wherein said fibrous material is produced by adding at least one selected from silver salts, copper salts and zinc salts to a carboxymethyl modified cellulose, followed by adding at least one selected from the group consisting of benzimidazole compounds, mercaptopyridine-N-oxide compounds, isothiazolone compounds, benzothiazole compounds and benzothiazolone compounds at a pH of 5 to 8.

25. A fibers material containing an antibacterial antifungal agent according to the above embodiment 24, wherein said fibrous material is produced by adding two or more selected from a silver salt, a copper salt and a zinc salt to a carboxymethyl modified cellulose, followed by adding at least one selected from the group consisting of benzimidazole compounds, mercaptopyridine-N-oxide compounds, isothiazolone compounds, benzothiazole compounds and benzothiazolone compounds at a pH of 5 to 8.

26. A fibers material containing an antibacterial antifungal agent according to the above embodiment 25, wherein said fibrous material is produced by adding three metal salts of a silver salt, a copper salt and a zinc salt to a carboxymethyl modified cellulose, followed by adding at least one selected from the group consisting of benzimidazole compounds, mercaptopyridine-N-oxide compounds, isothiazolone compounds, benzothiazole compounds and benzothiazolone compounds at a pH of 5 to 8.

27. A fibers material containing an antibacterial antifungal agent according to the above embodiment 26, wherein said fibrous material is produced by adding three metal salts of a silver salt, a copper salt and a zinc salt to a carboxymethyl modified cellulose, followed by adding a mercaptopyridine-N-oxide compound at a pH of 5 to 8.

28. A fibers material containing an antibacterial antifungal agent according to the above embodiment 27, wherein said fibrous material is produced by adding a silver salt to a carboxymethyl modified cellulose, then adding a mercaptopyridine-N-oxide compound to the resulting mixture at a pH of 5 to 8, followed by adding a copper salt, and then adding a mercaptopyridine-N-oxide compounds the resulting mixture at a pH of 5 to 8, followed by adding a zinc salt, and then adding a mercaptopyridine-N-oxide compound to the resulting mixture at a pH of 5 to 8.

29. A fibers material containing an antibacterial antifungal agent according to the above embodiment 26, wherein said fibrous material is produced by adding at least two of a silver salt, a copper salt and a zinc salt to a carboxymethyl modified cellulose, and then adding at least one compound selected from benzimidazole compounds, mercaptopyridine-N-oxide compounds, isothiazolone compounds, benzothiazole compounds and benzothiazolone compounds at a pH of 5 to 8, followed by adding a zinc salt.

30. A fibers material containing an antibacterial antifungal agent according to the above embodiment 29, wherein said fibrous material is produced by adding at least two of a silver salt, a copper salt and a zinc salt to a carboxymethyl modified cellulose, then adding a mercaptopyridine-N-oxide compound at a pH of 5 to 8, followed by adding a zinc salt.

31. A fibers material containing an antibacterial antifungal agent according to the above embodiment 26, wherein said fibrous material is produced by adding at least two of a silver salt, a copper salt and a zinc salt to a carboxymethyl modified cellulose, and then adding at least one compound selected from benzimidazole compounds, mercaptopyridine-N-oxide compounds, isothiazolone compounds, benzothiazole compounds and benzothiazolone compounds at a pH of 5 to 8, followed by adding a copper salt.

32. A fibers material containing an antibacterial antifungal agent according to the above embodiment 31, wherein said fibrous material is produced by adding at least two of a silver salt, a copper salt and a zinc salt to a carboxymethyl modified cellulose, then adding a mercaptopyridine-N-oxide compound at a pH of 5 to 8, followed by adding a copper salt.

33. The present invention is an antibacterial antifungal agent comprising a composite of organic compound containing at least one selected from sulfur atoms and heterocyclic rings with hetero-nitrogen atom and two or more metal salts selected from a silver salt, copper salt and a zinc salt.

34. The present invention is an antibacterial antifungal agent comprising a composite of organic compound containing at least one selected from sulfur atoms and heterocyclic rings with hetero-nitrogen atom and three metal salts of a silver salt, copper salt and a zinc salt.

35. The present invention is an article containing a fibrous material which contains an antibacterial antifungal agent comprising a metal salt of an organic compound.

36. An article according to the above embodiment 35, wherein said fibrous material is ion-exchange fibers.

37. An article according to the above embodiment 35, wherein said organic compound forming said organic metal salt is a compound containing at least one of sulfur atoms and heterocyclic rings with hetero-nitrogen atom.

38. An article according to the above embodiment 37, wherein said organic compound containing at least one of sulfur atoms and heterocyclic rings with hetero-nitrogen atom is at least one selected from the group consisting of benzimidazole compounds, mercaptopyridine-N-oxide compounds, isothiazolone compounds, benzothiazole compounds and benzothiazolone compounds.

39. An article according to the above embodiment 35, wherein said metal salt forming said organic metal salt is at least one selected from silver salts, copper salts and zinc salts.

40. An article according to the above embodiment 39, wherein said metal salt is a complex of two or more of a silver salt, a copper salt and a zinc salt.

41. An article according to the above embodiment 40, wherein said metal salt is a complex of three of a silver salt, a copper salt and a zinc salt.

42. An article according to the above embodiment 41, wherein said complex of three of a silver salt, a copper salt and a zinc salt has a composition of 10 to 40 silver, 20 to 60 zinc and the remainder copper by mole based on 100 moles of the total of metals, provided that copper is never zero.

43. An article according to the above embodiment 36, wherein said ion-exchange fibers are of at least one selected from polystyrenes, polyacrylics, polyamides, polyesters, polyethylenes and cellulose and having at least one of sulfonic acid group, phosphonic acid group and carboxylic acid group.

44. An article according to the above embodiment 43, wherein said ion-exchange fibers are carboxymethyl-modified fibers.

45. An article according to the above embodiment 44, wherein said ion-exchange fibers are carboxymethyl-modified cellulose fibers.

46. An article according to the above embodiment 45, wherein said carboxymethyl-modified cellulose fibers have a degree of modification as measured by a degree of substitution of 0.5 or less.

47. An article according to any one of the above embodiments 35 to 46, wherein said article comprises primarily the fibrous material containing an antibacterial antifungal agent of a metal salt of an organic compound, and organic fibers and/or inorganic fibers.

48. An article according to the above embodiments 47, wherein said organic fibers are alone or a composite of two or more selected from vegetable fibers, animal fibers, rayon, semi-synthetic fibers, and synthetic fibers.

49. An article according to the above embodiments 47, wherein said inorganic fibers are alone or a composite of two or more selected from glass fibers, carbon fibers, ceramic fibers and whiskers.

50. An article according to any one of the above embodiments 47 to 49, wherein said article comprises essentially the fibrous material containing an antibacterial antifungal agent of a metal salt of an organic compound and a material having an absorption function.

51. The present invention is a composite article consisting of a composite of an article comprising organic fibers and/or inorganic fibers and an article comprising a material having an absorption function, wherein at least one of the articles constituting said composite article contain an antibacterial antifungal agent of a metal salt of an organic compound.

52. An article adccording to the above embodiments 50 or 51, wherein said material having and absorption function is activated carbon and/or activated carbon fibers.

53. The present invention is a filter material using any one of articles according to any one of the above embodiments 35 to 52.

54. The present invention is an air filter using said filter material according to the above embodiment 53.

55. The present invention is an air filter for room conditioners using said filter material according to the above embodiment 53.

56. The present invention is an air filter for automobiles using said filter material according to the above embodiment 53.

57. The present invention is a wall material using any one of the materials according to any one of the above embodiments 35 to 52.

58. The present invention is an insole using any one of the materials according to any one of the above embodiments 35 to 52.

DETAILED DESCRIPTION OF THE INVENTION

The antibacterial antifungal agents and the fibrous materials according to the present invention will be explained in detail under.

The fibrous materials to be used in the present invention are generally of the form of fiber having a diameter of 0.1 to 100 $\mu$m.

In a preferred embodiment of the present invention, the antibacterial antifungal agents should be provided firmly and densely within the structure of the fibers and/or on the surfaces thereof. In order to allow the antibacterial antifungal agent to effectively act, the fibers must have proper swelling property, ion-permeability, and ion-capturing property.

As fibers as above, so-called ion-exchange fibers may be used. For example, the materials for the fibers can be obtained by introducing appropriately at least one of sulfonic acid groups, phosphonic acid groups and carboxylic acids into a base polymer such as polystyrenes, polyacrylics, polyamides, polyethylenes, and cellulose.

Nature cellulose fibers as called generally "pulp" may be transformed partly by chemical modification into preferred fibers to be used. The chemical modification includes sulfation, phosphation, nitration, carboxymethylation, carboxyethylation, and carboxypropylation. Among them, carboxymethylation is extremely preferred for practicing the present invention because it can be conveniently performed at low cost and high safety to produce fibers which are excellent in swelling property and ion-permeability. Particularly partially modified cellulose fibers having a degree of substitution of 0.5 or less are most preferred.

Pulps as starting materials for carboxymethylated fibers to be preferably used in the present invention include properly carboxymethylated wood pulps (e.g., hardwood pulp and softwood pulp). Besides regenerated cellulose such as rayon may similarly be used. Moreover, synthetic fibers having ion-exchange ability which are properly modified in the same manner as described above, arginic acid fibers, and wet spun fibers of water soluble polymers may similarly be used. Wet spun fibers produced from a polymer liquid containing an organic metal salt complex having an antibacterial antifungal activity according to the present invention also may be used.

In one embodiment of the present invention, preferred fibers can be achieved by carboxymethylation of nature cellulose fibers.

Production of carboxymethylated pulps has already established in the art and can be performed by either an aqueous medium method or an solvent method as described in, for example, "Development of functional cellulose" published from CMC Co. on Aug. 30, 1985 pp. 60 to 61.

Fiber materials having a desired degree of carboxymethylation can be obtained basically by controlling an amount of sodium monochloracetate, an amount of alkali and an amount of water relative to cellulose fibers and other reaction conditions.

Generally a degree of substitution with carboxymethyl group (which is synonymous with a degree of carboxymethylation) is defined by a degree of substitution with carboxymethyl group per glucose unit and a substitution rate can be determined by transforming first into an acid type of carboxymethyl-cellulose and then neutralizing with an addition of excess amount of alkali, followed by back titration with acid.

The fibrous materials having varying degrees of carboxymethylation to be used in the present invention have a higher metal-ion-capturing ability with an increase in the degree of substitution to be capable of having a higher concentration of the organic metal salt complex having an antibacterial antifungal activity of the present invention filled in the fibers. At a much higher degree of substitution, excess swelling is caused resulting in a reduction in the fiber strength with reaching solubilization of the fibers, which is undesired in the practice of the present invention. Generally the fibrous materials become soluble at a degree of substitution of about 0.6. An upper limit of the degree of substitution is about 0.5 for keeping the fibrous shape though the strength is reduced and the degree of substitution is preferably 0.5 or less.

In a preferred embodiment of the present invention, it is difficult to define a lower limit of the degree of substitution for cellulose fibers. For example, experimental results show that carboxy-methylated pulps having a degree of substitution of 0.4 can capture 2.5 mmol monovalent metal ions per gram, but that in order to form the less releasable complexes within the fibers and at least on and around the surfaces of the fibers by capturing practically effective amounts of metal ions and by subsequent reactions with organic compounds, it is proper to set the degree of substitution at about 50% of the ion-exchange capacity.

Therefore, with carboxymethylated pulps having a degree of substitution of 0.5, there can be formed an amount of 1 to 1.5 mmol of organic metal salt complex/gram. This indicates that if the organic metal salt complex has a molecular weight of 150 to 250, an antibacterial antifungal agent is formed at about 15 to 40% solids which is sufficient to achieve an antibacterial antifungal activity.

Pulp itself can exhibit sufficient antibacterial antifungal activity at a concentration of the antibacterial antifungal agent of about 1% by weight solids based on the pulp or even at a lower concentration. This may be considered to indicate that even modifications at considerably lower degrees of substitution can be useful. In an embodiment, the antibacterial antifungal pulps processed as above may be used as a so-called master batch in the resin industry which may partly be mixed with other starting fibers by using a wire paper machine, a cylinder paper machine, an inclined paper machine, or a combination thereof. This embodiment allows the pulps to be commercially applied to various articles, especially to filter materials, which are easily manageable and extremely practical.

In order to have such utilities, such a degree of substitution as enabling the pulps to contain an antibacterial antifungal agent at a concentration of 1% or more, preferably 5% or more, most preferably 5 to 30% by weight solids based on the pulps is required. For the purpose, those having a degree of substitution of at least 0.2 (generally not more than 0.5), preferably 0.35 or higher (generally not more than 0.5) are desired.

The metal ion substituting treatment and the organic compound treatment may be repeated twice or more instead of once, thereby allowing a higher content of an antibacterial antifungal agent to be filled in the fibers.

Therefore, a lower degree of substitution than the ranges as described above is not excluded.

The content of an antibacterial antifungal agent in the pulps according to the present invention should preferably be 1% by weight, more preferably 5% or more, most preferably 5 to 30%. If it is over the range, degradation in fiber strength and release of the antibacterial antifungal agent from the fibers may undesirably be caused.

As described in the previous paragraph, the use of a part of the pulps having a high concentration of an antibacterial antifungal agent filled has advantages as stated below. Comparison of an article comprising a uniform distribution of a pulp having a lower concentration of an antibacterial antifungal agent filled therein with the same article, except that it comprises a speckle distribution of a pulp having a higher concentration of the agent indicates that the latter is evidently superior in resistance to a high concentration of bacteria and durability.

It is a well-known fact that there coexist in nature various resistant bacteria as well as sundry bacteria. In order to exhibit an effectiveness inhibiting all of those bacteria, the land distribution of an extremely concentrated antibacterial antifungal agent is very effective and economical means.

Various sheet-like articles using the fiber materials containing the antibacterial antifungal agents of the present invention also have excellent antibacterial and antifungal functions. They may be used for various articles, for example, filter materials, especially most suitable for automobile air filters. The fibrous materials according to the present invention are outstanding not only in an initial antibacterial antifungal activity, but also in sustained antibacterial antifungal activity. Therefore, they can remove unique mold odor which a driver may experience when he gets on a car or he actuates a car conditioner, and they can sustain such function for an extended period of time. The fibrous materials containing the antibacterial antifungal agents according to the present invention can be used for wall materials and insole with excellent antibacterial antifungal functions being exhibited.

For organic and/or inorganic fibers to be used in combination with the fibrous materials of the present invention, the organic fibers include alone or a mixture selected from vegetable fibers, animal fibers, regenerated fibers, semi-synthetic fibers and synthetic fibers, while the inorganic fibers include alone or a mixture selected from glass fibers, carbon fibers, ceramic fibers and whiskers.

The vegetable fibers include cotton and flax (flax plant, ramie) fibers. The animal fibers include silk and wool fibers.

The regenerated fibers include rayon and cuprammonium rayon. The semi-synthetic fibers include acetate, triacetate and Promix fibers. The synthetic fibers include nylon, acryl, vinylon, vinylidene, polyvinyl chloride, polyester, polyethylene, polypropylene, benzoate, Polychlal and phenol fibers The definition of fibers in the present invention as described above is based on "FIBER HANDBOOK" (edited 1993).

The fibers to be used in the present invention include wood pulps such as soft pulp and hard pulp, arbor pulps and grass pulps such as straw pulp. Pulps from used paper and broken paper may also be used.

An embodiment of the process for producing the fibrous materials containing the antibacterial antifungal agents which comprises steps of adding metal salts to ion-exchange fibers and then adding organic compounds the resulting fibers will be described under with regarding metal ion substitution treatment of partly carboxymethlated fibrous materials and antibacterial antifungal organic compounds.

An example with a Na-type carboxymethyl cellulose having a degree of substitution of 0.4 will be explained:

1) Adding water to 100 grams solids of the aforementioned pulp to such an extent as enabling stirring,
2) Adding 100 mmol of silver nitrate (17 grams),
3) Adding an alkali to achieve pH of 5.5 to 6.0 in the system,
4) Stirring for 30 minutes at room temperature to effect sufficient substitution (adsorption),
5) Adding 1000 milliliters of a 0.1 M/L sodium 2-mercaptopyridine-N-oxide solution in portions with stirring, The end point of the reaction can be detected by measuring a potential with silver electrodes or platinum electrodes.

6) After finished adding, stirring is conducted for additional 30 minutes to effect sufficient reaction.
7) Adding a 0.1 M/L sulfuric acid to lower pH of the system to 4, and then dewatered with a press.

According to the above procedure, the pulp containing silver mercaptopyridine-N-oxide can be obtained. If necessary, the pulp is redispersed in water and washed to previously remove released portions. It has been found from the results of the experiments that the salts are formed in the form fixed within and on the surfaces of the fibers at a yield of 90% or more, though a part of the salts may be released.

In order to form the silver mercaptopyridine-N-oxide within or on the surfaces at high yield, pH control, stirring, concentration and rate of reagents to be added are required to be optimized.

A process for producing a complex of organic compound exhibiting most effectively antibacterial and antifungal functions will be described.

Basically in the same manner as in the case of single metal salt as described above, a metal salt composition to be added to carboxymethyl cellulose can be obtained by formulating according to calculation, and reactions with respective ions can be monitored by potential measurement with silver or platinum electrodes.

In an embodiment, a process for producing a complex of 2-mercaptopyridine-N-oxide may be illustrated by adding 2-mercaptopyridine-N-oxide to a complex system of silver, copper and zinc.

A practical formulation for forming a complex consisting of 25 mol % silver, 25 mol % copper and zinc 50% and 2-mercaptopyridine-N-oxide is as follows: Na-type carboxymethyl cellulose

| | | |
|---|---|---|
| (DS = 0.4) solids | 100 | grams |
| water | 5000 | grams |
| silver nitrate | 25 | mmol |
| copper sulfate | 15 | mmol |
| zinc nitrate | 30 | mmol |
| water | 1000 | grams |
| 0.1M/L sodium 2-mercaptopyridine-N-oxide solution | 1000 | grams |

In a preferred embodiment of the present invention, the production of a complex can be achieved by various adding procedures, for example, an addition of silver nitrate→addition of 2-mercaptopyridine-N-oxide compound→addition of copper sulfate→addition of 2-mercaptopyridine-N-oxide compound→addition of zinc nitrate→addition of 2-mercaptopyridine-N-oxide compound.

Heterocyclic compounds with hetero-nitrogen atom and sulfur-containing compounds such as thiol compounds and thion compounds can be produced on the basis of the same concept.

Iso-thiazoline-3-one compounds are also useful and many of imidazole derivatives themselves have (antibacterial) antifungal activity with 2-(4-thiazolil)benzimidazole (TBZ) being well known.

These compounds have a low water solubility and they can not be added in the form of aqueous solution. However, they are soluble into organic solvents which are miscible with water, for example, alcohols, glycols, dimethylsulfoxide (DMSO), and they can be added as a solution in these solvents, thereby forming metal salts within pulps.

In an embodiment for practicing the present invention, an reduction in pH as described in the case of Na-type carboxymethyl cellulose having a degree of substitution of 0.4 is for suppressing excess swelling of pulp, and therefore it is not critical.

Another method for suppressing the swelling is to add multivalent metal ions with great effects. Addition of salts of aluminum, magnesium, zirconium, silicates, zinc, and copper are effective. Among them, the addition of zinc ions and copper ions which themselves have antibacterial and antifungal functions provides additional functions as absorbents of ammonia, amines, sulfide gases. Another benefits of adding excess copper ions are to cause discoloration upon the absorption of the gases which is useful for discoloration display (indicator) application.

The fibrous materials containing antibacterial antifungal agents according to the present invention overcome the aforementioned problems and exhibit various excellent effects as follows:

(1) Very effective to inhibit both bacteria and mold, (2) Good at working to a high concentration of bacteria contaminants, (3) Excellent in durability, (4) Extremely less reduction in effect due to washing with water, (5) Less soluble and highly stable.

(6) Very low volatility, extremely less release contamination, extremely effective to inhibit both bacteria and mold.

The fibrous materials of the present invention can be applied to various articles in the form of various sheets, for example, various filter materials, practically not only various air filters, but also filter materials for discharge processing machines, those for water treatment and those for filtering liquids such as crankcase oil and fuel.

The fibrous materials of the present invention may be used as a part of the component fibers of the filter materials consisting of various synthetic fibers and synthetic binders as disclosed in Japanese Patent Application No. Hei 7-20315 titled "Filter materials and process for producing the same", whereby filter materials which can exhibit excellent effects to inhibit both bacteria and mold without depressing the functions of filter materials can be provided.

The fibrous materials of the present invention may be used as a part of the component fibers of the filter materials consisting of specific acrylic fibers, metal cross-linked fibers and fibrillated organic fibers as disclosed in Japanese Patent Application No. Hei 7-221247 filed by the present applicant and titled "Filter materials and air filter", whereby filter materials which can exhibit excellent effects to inhibit both bacteria and mold without depressing the functions of filter materials can be provided.

The fibrous materials of the present invention may be used in the glass fiber sheets for air filter made of a mixture of specific glass fibers as disclosed in Japanese Patent KOKAI No. Hei 5-123513, whereby filter materials which can exhibit excellent effects to inhibit both bacteria and mold without depressing the functions of filter materials can be provided.

The fibrous materials of the present invention may be used in the deodorizing fiber comprising fiber sheets, at least one of which contains thermoplastic fibers, having particulate deodorizer (activated coconut shell carbon particles) sandwiched therebetween fused by partial supersonic melting as disclosed in Japanese Patent KOKAI No. Hei 7-163818, whereby filter materials which can exhibit excellent effects to inhibit both bacteria and mold without depressing the functions of filter materials can be provided.

The fibrous materials of the present invention may be used in at least one layer of the three layer structure filter materials for air cleaner consisting of an outer layer comprising primarily hydrophobic fibers, an intermediate layer comprising a high density fiber structure, and an innermost layer comprising a high density non-woven fabric, said respective layers being impregnated with polyester resin as disclosed in Japanese Patent KOKAI No. Hei 6-343809, whereby filter materials which can exhibit excellent effects to inhibit both bacteria and mold without depressing the functions of filter materials can be provided.

The fibrous materials of the present invention may be formed alone into sheet-like articles which may be used for filter materials. More practically they may be mixed with other various compatible fibers and then the mixture may be made into filter materials. As described above, the antibacterial antifungal agents are absorbed at high concentrations on fibrous materials to prepare a master batch and then the master batch may be applied to produce the fibrous materials of the present invention. This procedure is more effective and has great advantages on production work.

The filter materials using the fibrous materials of the present invention can employ organic fibers and/or inorganic fibers of a very fine diameter to improve capture efficiency.

Fine fibers to be used in the present invention include preferably those having an average diameter of 5 $\mu$m or less, without being specifically limited thereto, organic fibers, inorganic fibers and fillers. Among them, fine fibers such as micro-glass fibers having an average diameter of 3 $\mu$m or less or organic fibers, a part of which is fibrillated to have a diameter of 1 $\mu$m or less are more preferred.

Generally micro-glass fibers refer to ultrafine fibers having an average diameter of 5 $\mu$m or less which are produced by vapor spraying, spinning, flame intervening, a rotary method or the like. In the present invention, those of 3 $\mu$m or less are preferred.

The organic fibers, a part of which is fibrillated to a fiber diameter of 1 $\mu$m or less include those processed by the following methods:

1) A solution of synthetic polymer is allowed to flow down into a poor solvent under shearing force to precipitate fibrillated fibers (Fibrid process, Japanese Patent Publication No. Sho 35-11851).

2) Synthetic monomers are polymerized under shearing force to precipitate fibrils (Shearing polymerization process, Japanese Patent Publication No. Sho 47-21898).

3) Two or more non-compatible polymers are mixed, melt-extruded or spun, cut, and then fibrillated by mechanical means into fibers (Split process, Japanese Patent Publication No. Sho 35-9651).

4) Two or more non-compatible polymers are mixed, melt-extruded or spun, cut, then immersed in a solvent to dissolve one polymer, and fibrillated into fibers (Polymer blend dissolving process, U.S. Pat. No. 3,382,305).

5) Synthetic polymers are explosively spouted out from high pressure side to low pressure side at temperatures higher than the boiling point of the solvent and then fibrillated (Flash spinning process, Japanese Patent Publication No. Sho 36-16460).

6) Fibers are cut to an appropriate length, dispersed in water, and fibrillated with a homogenizer or beater (Japanese Patent KOKAI No. Sho 56-100801 and Japanese Patent KOKAI No. Sho 59-92011).

Commercially available fibrillated organic fibers include KY-400S, poly-p-phenyleneterephthalamide fibrils which are produced by fibrillating the fibers with a homogenizer (mfd. by Daicel Chemical Industry), Cerish KY-100S, pulp fibrils which are produced by fibrillating the pulp with a homogenizer (mfd. by Daicel Chemical Industry), PC-310S, linter fibrils which are produced by fibrillating the linter with a homogenizer (mfd. by Daicel Chemical Industry), KY-410S, acrylic fibrils which are produced by fibrillating the acrylic fibers with a homogenizer (mfd. by Daicel Chemical Industry), KY-420S, polyethylene fibrils which are produced by fibrillating the polyethylene fibers with a homogenizer (mfd. by Daicel Chemical Industry), and KY-430S, polypropylene fibrils which are produced by fibrillating the polypropylene fibers with a homogenizer (mfd. by Daicel Chemical Industry). Moreover, fibrillated fibers produced by fibrillating cellulose staple (tradename, Lyocell) from Courtaulds Co. with a beater or disk refiner may be referred to.

When the fibrous materials of the present invention are mixed and used with various other fibers, various binders can be used, if necessary.

Fibrous binders to be used in the present invention include composite fibers such as core-sheath type (core-shell type), and parallel type (side by side type). For example, a combination of polypropylenes (core) and polyethylenes (sheath) (tradename: Daiwabo NBF-H; product of Daiwaboseki), a combination of polypropylenes (core) and ethylenevinylalcohol (sheath) (tradename: Daiwabo NBF-E; product of Daiwaboseki), a combination of polypropylenes (core) and polyethylenes (sheath) (tradename: Chisso ESC; product of Chisso), a combination of high melting point polyesters (core) and low melting point polyesters (sheath) (tradename: Melty 4080; product of Unitika) may be referred to. Moreover, thermally water-solubilizable type such as vinylone binder fibers (VPB 107×1; product of Kuraray) may be used.

The diameter of binder fibers is not critical, but a diameter of 0.3 to 5 denier is preferred, and 1 to 2 denier is more preferred. If the diameter is lower than 0.3 denier, pressure loss through filters becomes higher with the useful life of filters being short. If the diameter is larger than 5 denier, there may be formed voids between stepwise distributed filters in filter materials resulting in a loss of capturing efficiency. And a reduction in fused area contacting with other fibers may be caused with less increase in filter strength.

Incorporation of fibrous binders can impart good tensile strength and fold flexibility to sheets at the time of production thereof, whereby it can increase internal strength of filter materials, and take a role of preventing sheet breaking which may be caused at steps of adding a water repellent and a binder and of slitting when a tension is applied, and also preventing surface spalling which may be caused at steps of slitting and pleat processing when the filter materials are rubbed.

When the fibrous materials of the present invention are produced by wet sheet making process, it is required for making the texture better that various filters such as synthetic filters, fibrillated organic filters, and fibrous binders are uniformly dispersed in water in a dispersion tank such as pulper. For this purpose the use of surfactants is desired.

The surfactants may be divided into anionic, cationic, non-ionic and amphoteric surfactants. Anionic surfactants include, for example, carboxylates, sulfates, sulfonates, and phosphates. Cationic surfactants include amine salts and ammonium salts. Non-ionic surfactants include ether type, ester type and amino-ether type surfactants. Amphoteric surfactants include betaine type surfactants. Among them, those capable of providing better dispersion of fibers may optionally be selected to be used. It is no problem to use other surfactants than those described above if they can provide good dispersion.

The dispersion stability of a uniformly dispersed fiber mixture may be improved by adding an anionic polyacrylamide thickener to a fiber dispersion liquid or to a sheet making head, thereby improving further the texture of filter materials after wet-made into sheets.

The filter materials of the present invention may be produced in the form of single layer or two or more multi-layer by means of wet sheet making machines such as a wire paper machine, a cylinder paper machine, an inclined wire paper machine, or a combination of the same type or different types. In the case of two or more layers, it is possible to elongate the life of the filters by making the layer facing upstream rough, while making the layer facing downstream dense.

For drying, cylindrical dryer, through dryer, infrared dryer and the like may be used.

The filter materials of the present invention have good strength and toughness just after made into sheets and dried. In order improve further the strength and toughness, it is possible to add various binders after wet making sheets and drying.

The binders include, for example, acrylic latex, vinylacetate latex, urethane latex, epoxy latex, polyester latex, SBR latex, NBR latex, epoxy binders, phenolic binders, PVA, starch, and paper fortifiers used generally in paper making processes. These may be used alone or in combination with cross linking agents.

An amount of binders to be added after making and drying sheets is less than 20% by weight based on the weight of filter materials. The amount over 20% by weight may cause a reduction in capturing ability as well as an increase in loss of pressure with shortening the life, though the strength and toughness may be enhanced.

To the filter materials may be added water-repellants and flame-retardants.

DESCRIPTION OF PREFERRED EMBODIMENTS

The present invention, that is, fibrous materials containing an antibacterial antifungal agent and a process for producing the same will be described in detail with reference to examples without being limited thereto.

EXAMPLE 1

(1) Production of Modified Pulps Having Different Degrees of Carboxymethylation (DS)

To 162 grams (based on the weight of solids) NBK pulp were added 49 grams caustic soda, one liter iso-propyl alcohol and 100 milliliters water, and the mixture was stirred at ordinary temperature for about 30 minutes, and 70 grams sodium monochloracetate were added to the mixture. Then the temperature was raised up to 70° to 80° C. and the mixture was reacted for 2 hours. After cooling, filtrating and dewater-pressing, one liter of a mix liquid of water and iso-propyl alcohol at a ratio of 1:1 was added to the reaction product which was acidified with sulfuric acid to pH 3.5, stirred for 2 hours. The product was filtered and washed with water twice and dewatered.

A part of sample was measured for a degree of carboxymethylation (DS) after transformed into an acid type by treating with an aqueous solution of sulfuric acid of a pH of about one.

The sample had a DS=0.48. This is referred to as Modified pulp A.

The same procedure was repeated, except that an amount of sodium monochloracetate was varied, to produce pulps having different DS. The amount of sodium monochloracetate used and DSs of produced modified pulps are shown in Table below:

| Modified pulp | Amount of sodium monochloracetate (gr.) | DS |
| --- | --- | --- |
| B | 60 | 0.38 |
| C | 50 | 0.22 |
| D | 40 | 0.12 |

(2) Absorption of Ag Ions on Carboxymethylated Pulps

The modified pulps A to D as prepared above and untreated pulp were measured for an amount of Ag ions to be adsorbed on the pulps. One gram of each pulp on dryness was dispersed in 100 milliliters of water, to which 5 milliliters of a 1 N silver nitrate solution were added, adjusted to pH 5.5, stirred at room temperature for 2 hours, and filtered.

The filtrate was determined for silver adsorption by potentiometric titration with a solution of potassium iodide. The results obtained are shown in Table below.

|  | DS | Ag ion adsorption mmol/g |
| --- | --- | --- |
| Modified pulp A | 0.48 | 2.84 |
| Modified pulp B | 0.38 | 2.26 |
| Modified pulp C | 0.22 | 1.13 |
| Modified pulp D | 0.12 | 0.66 |
| Unmodified pulp | — | 0.013 |

The amount of Ag ion adsorption (the amount of substitution) was almost coincident with the expected value from DS by calculation, though it was slightly lower than the latter. Thus, it was confirmed that the adsorption depends on DS. Untreated pulps also exhibited some adsorption.

The degree of swelling becomes higher with the degree of carboxymethylation. The modified pulp A was significantly swelled when the pH was adjusted to 5.5, and microscopic observations indicated that the pulp kept the form of fiber. In this Example, a DS of about 0.5 could be considered to be a limit for the pulps to keep the form of fiber without any other specific treatment (any one of various prior art processes such as cross-linking with epichlorohydrin to transform an inherently soluble pulp into a soluble one).

(3) Production of Ag Ion Adsorbed (Substituted) Pulp, 2-Mercaptopyridine-N-Oxide Complex Pulp and Sheets Using the Same Silver Adsorbed Pulp (Comparative Example)

10 grams on dryness of one of the modified pulps A to D as prepared above and untreated pulp were measured, dispersed in 500 milliliters of water, to which a 1 N silver nitrate solution was added, and adjusted to pH 5.5. The amount of silver nitrtate added was about a half the saturated adsorption amount obtained from the previous experiments.

|  |  | Amount of N—$AgNO_3$ added |
| --- | --- | --- |
| Modified pulp A | 10 grams | 15.0 |
| Modified pulp B | 10 grams | 10.0 |
| Modified pulp C | 10 grams | 5.0 |
| Modified pulp D | 10 grams | 3.0 |
| Unmodified pulp | 10 grams | 3.0 |

The unmodified pulp had a very low Ag ion adsorption, to which sufficiently excess amount of silver nitrtate was added. the mixture was stirred at room temperature for 30 minutes, filtered, redispersed in 500 milliliters, and washed with water.

These were made silver adsorbed pulps and referred to as described below. They are comparative examples.

| |
| --- |
| CP48Ag |
| CP38Ag |
| CP22Ag |
| CP12Ag |
| PAg |

Note;
CP: Modified pulp
Number: Relative DS value
P: Unmodified pulp (4) Production of Ag/2-Mercaptopyridine-N-Oxide Complex Pulp In the same procedure as in the production of silver adsor bed p ulps described above, to each pulp solution was added silver nitrtate, and the mixture was adjusted to pH 5.5, and stirred for 30 minutes. 0.1 M/L sodium 2-mercaptopyridine-N-oxide solution (referred to as MP by abbreviation) was added to each pulp dispersion in an equimolar amount as the amount of silver nitrtate added. After stirring for 30 minutes, the pH was lowered to 4 with sulfuric acid, and the product was dewatered.

The waters from the dewatering of the pulp batches A to D were slightly cloudy, while those from the unmodified pulp were relatively highly clouded in white (which indicated many reactions occurred outside pulp fibers).

Again 500 milliliters of water were added to the dewatered pulp, stirred, washed with water, and then dewatered. These are referred to as silver-MP-modified pulps and designated as follows:

| | |
| --- | --- |
| CP48AgMP | Present invention |
| CP38AgMP | Present invention |
| CP22AgMP | Present invention |
| CP12AgMP | Present invention |
| PAgPM | Comparative Example |

(5) Production of Antibacterial Antifungal Sheet 10 parts by weight of each of the processed pulps and the pulp of the comparative example as above and 90 parts by weight of NBKP untreated pulp were mixed in an appropriate amount of water and beaten with a mixer. The resulting pulp were made into sheets 100 g/$m^2$ in basis weight with TAPPI standard paper making hand machine. Antibacterial antifungal sheets containing 10 grams of one of the thus obtained processed pulps and comparative example pulp were evaluated for antibacterial antifungal activities.

Test method—① (Antibacterial (Bactericidal) Activity)

Colibacillus (E-coli IFO 3301) were cultivated in a liquid culture ground (peptone yeast) for 24 hours, and diluted to prepare a test liquid of $2 \times 10^8$ cell/mL.

Cut test specimens of 2 cm×2 cm were placed on Petri dish and the bacteria liquid as prepared above was added to the dish by dropping 5 drops (about 0.1 milliliter) of the liquid with Pasteur pipette. The dish was covered not to dry and maintained at 38° C. for 24 hours.

Thereafter, each test specimen was pressed onto the Nutrient Broth agar culture ground to transfer the bacteria on the test specimen to the ground and then removed. The ground was cultured again at 38° C. for 24 hours, and observed.

Evaluation was graded as follows:

Almost completely destroyed bacteria with no growth of bacteria

Almost completely destroyed bacteria with growth of 5 or less colonies on the transferred surface of 2 cm×2 cm.

+ Good antibacterial and antifungal activities with growth of 100 colonies or less on the transferred surface of 2 cm×2 cm.

++ Weak or lower antibacterial and antifungal activities with an effect being observed on the transferred surface of 2 cm×2 cm.

+++ NO practical effect observed on the transferred surface of 2 cm×2 cm.

Test Method—② (Antifungal Activity)

Bread mold (*Aspergillus niger*) was used as test strain. 5 platinum earpicks of bacterial spores were taken from an inclined culture ground, to which a small amount of a wetting agent (a solution of sodium dioctyl sulfosuccinate) was added and vigorously shaken to disperse the spores, filtrated with gauze and the whole amount was adjusted to 50 milliliters.

A GP culture ground (mfd. by Nippon Pharmaceutical Co) with an addition of 1.5% agar was prepared, sprayed uniformly with the bacteria liquid as prepared above, dried once over the surface thereof, on which cut specimens of 2 cm×2 cm were placed, sufficiently fixed under pressure, again sprayed over all the surface with the bacteria liquid, cultivated at 28° C. for a certain period of time up to four weeks while observing with time.

Evaluation was graded as follows:

Completely inhibited the growth of mold.

Uncertain growth of mold.

Considerably good antifungal activity with growth of mold in an area of ⅕ or less of all the surface.

++ Evident growth of mold in an area of about ⅓ of all the surface.

+++ Evident growth of mold all over the surface.

The results of the above tests for antibacterial activity and antifungal activity are shown in Tables 1 and 2 below, respectively.

TABLE 1

| Sample No. | Sample content | | Antibacterial (bactericidal) activity Colibacillus (*E-coli*) |
|---|---|---|---|
| 1 | P (NBKP 100%) | Comp. Ex. | +++ |
| 2 | PAg 10% containing sheet | Comp. Ex. | ++ |
| 3 | CP12Ag 10% containing sheet | Comp. Ex. | - |
| 4 | CP22Ag 10% containing sheet | Comp. Ex. | - |
| 5 | CP38Ag 10% containing sheet | Comp. Ex. | - |
| 6 | CP48Ag 10% containing sheet | Comp. Ex. | - |
| 7 | PAgMP 10% containing sheet | Comp. Ex. | ++ |
| 8 | CP12AgMP 10% containing sheet | Present Invention | - |
| 9 | CP22AgMP 10% containing sheet | Present Invention | - |
| 10 | CP38AgMP 10% containing sheet | Present Invention | - |
| 11 | CP48AgMP 10% containing sheet | Present Invention | - |

TABLE 2

| Sample No. | Sample content | | Antifungal (*ASPERGILLUSNIGER*) activity after | | |
|---|---|---|---|---|---|
| | | | 5 days | 2 weeks | 4 weeks |
| 1 | P (NBKP 100%) | Comp. Ex. | +++ | +++ | +++ |
| 2 | PAg 10% containing sheet | Comp. Ex. | ++ | +++ | +++ |
| 3 | CP12Ag 10% containing sheet | Comp. Ex. | ++ | +++ | +++ |
| 4 | CP22Ag 10% containing sheet | Comp. Ex. | + | ++ | +++ |
| 5 | CP38Ag 10% containing sheet | Comp. Ex. | - | ++ | +++ |
| 6 | CP48Ag 10% containing sheet | Comp. Ex. | - | ++ | +++ |
| 7 | PAgM 10% containing sheet | Comp. Ex. | - | ++ | +++ |
| 8 | CP12AgMP 10% containing sheet | Present Invention | -- | + | + |
| 9 | CP22AgMP 10% containing sheet | Present Invention | -- | - | - |
| 10 | CP38AgMP 10% containing sheet | Present Invention | -- | - | - |
| 11 | CP48AgMP 10% containing sheet | Present Invention | -- | - | - |

The results from Tables 1 and 2 brings to the following conclusion:

Silver ions act very effectively to Colibacillus. Even the sheets simply contacted with Ag ions without chemical modification (Sample No. 2) were appreciated to exhibit some effects, and modified pulps of Sample Nos. 3 to 6 exhibited evident effects.

However, silver ions have little or no practical antifungal effects, though they have initially a little inhibition activity.

On the other hand, all of the CPAGMP system sheets exhibited good results (Sample Nos. 8 to 11). Particularly Sample Nos. 9 to 11 provided extremely good results in antibacterial (bactericidal) activity as well as in antifungal activity even in the long term tests more than 2 weeks.

EXAMPLE 2

(1) Product Ion of Various Metal Salt Adsorbed Pulps and MP Pulps

The same procedure as in the production of modified pulp B in Example 1 was repeated to produce a sample pulp. This had a DS of 0.40. The resulting carboxymethylated pulp was designated as CP 40. The pulp was evaluated for swelling property in water. A part of the pulp was redispersed in water and acidified to pH 4 with sulfuric acid, and another redispersion of part of the pulp was adjusted to pH 6 with caustic soda, which were determined for solids contents after dewatered by pressing to have 19.5% and 6.6%, respectively. It have been found that incorporation of carboxyl group allows significant swelling with transform from H-type to Na-type. Moreover, microscopic observations indicated that Na-type fibers underwent an entire swelling as well as spherically bulky swelling with maintaining sufficiently the form of fiber.

To 10 grams on dryness of CP 40 were added 500 millimeters of water to disperse the fibers. 10 millimeters of a 1 N silver nitrate solution were added to the dispersion, which was adjusted to pH 5.5 and stirred for 30 minutes. Thereafter, 100 millimeters of a 0.1 M/L MP solution were added to the dispersion, stirred for 30 minutes. The dispersion was adjusted to lower its pH to 4, then dewatered, washed with water and again dewatered. This was designated as Sample No. 27, CP40AgMP.

Sample Nos. 28 and 29 were prepared in the same manner as above, except that copper sulfate and zinc nitrate solutions were respectively used instead of silver nitrate. Sample No. 30 was prepared in the same manner as above, except that 5 millimeters of a 1 N silver nitrate solution and a 1 N copper sulfate solution were added, and designated as CP40Ag50Cu50MP.

Sample Nos. 31 and 32 were also prepared with a combination of two sorts of metal ions. Sample No. 33 was prepared with a combination of three sorts of metal ions. In these cases, 2.5 millimeters of a 1 N silver nitrate solution, 3.0 millimeters of a 1 N copper sulfate solution and 5.0 millimeters of a 1 N zinc nitrate solution were u sed t o be added.

TABLE 3

| Sample No. | Sample pulp designation | |
|---|---|---|
| 21 | CP40 | Comparative Example |
| 22 | CP40C1BZ | Comparative Example |
| 23 | CP40MP | Comparative Example |
| 24 | CP40Ag | Comparative Example |
| 25 | CP40Cu | Comparative Example |
| 26 | CP40Zn | Comparative Example |
| 27 | CP40AgMP | Present Invention |
| 28 | CP40CuMP | Present Invention |
| 29 | CP40ZnMP | Present Invention |
| 30 | CP40Ag50Cu50MP | Present Invention |
| 31 | CP40Ag50Zn50MP | Present Invention |
| 32 | CP40Cu50Zn50MP | Present Invention |
| 33 | CP40Ag25Cu25Zn50MP | Present Invention |

Comparative Example, Sample No. 21 was an pulp having a DS of 0.40.

Comparative Example, Sample No. 22 was a pulp preared by adding 100 millimeters of a 0.1 M/L benzalkonium chloride solution based on 10 grams of carboxymethylated pulp, adjusting its pH to 5.5, stirring, dewatering, washing with water and then again dewatering in the same manner as described above.

Comparative Example, Sample No. 23 was a pulp prepared, identically to the above, by adding 100 millimeters of a 0.1 M/L MP solution based on 10 grams of carboxymethylated pulp, adjusting its pH to 5.5, stirring, dewatering, washing with water and then again dewatering.

Comparative Examples, Sample Nos. 24, 25 and 26 were prepared corresponding to Sample Nos. 27, 28 and 29 by omitting the addition of the MP solution and the pH adjustment with sulfuric acid.

The number shown after the metal atom represents the molar proportion.

(2) Production of Water Resistant Sheets 50 parts by weight of polyester fibers of 0.5 denier and 5 mm long (mfd. by Teijin Co.) and 40 parts by weight of heatmelt type binder fibers of 2 denier and 5 mm long (mfd. by Unitika Co.) were mixed with an appropriate amount of water, beaten with a mixer, mixed with 10 parts by weight of one of the pulps prepared as above including comparative example pulps, again blended, beaten, and then the dispersion was spread on a filter sheet using a Buchner funnel, dewatered, and then formed into sheets. The sheets were pressed and dried with a domestic iron at about 120° C. . The basis weight was 100 g/m². In this way, there were produced sheets which were not dissoluble even in water.

In addition to the test methods ① and ②, practical evaluation was made by employing the following test methods.

The sheets were also evaluated for durability by determining antibacterial and antifungal activities after effecting the treatments as described under.

1) UV resistance . . . Irradiated at a distance of 10 cm under a 100 W high pressure mercury lamp for 8 hours three times to give 24 hours irradiation in total.

2) Heat resistance test . . . At 100° C. for 10 hours.

3) Resistance to washing test . . . Washing in tapping water for 2 days.

4) Mud-immersion test . . . Immersing specimens in a suspension of 100 grams of a surface layer of the soil in the laboratory lot in 500 milliliters of water for one month.

Test Method—③ (Repeated Immersion Test in a Liquid of Colibacillus)

Similarly to Shake flask method, to a 100 mL triangular flask was added 20 milliliters of a solution, which was prepared by diluting a 0.5 M/L $KH_2PO_4$ solution 800 times, to which 2 milliliters of the bacteria solution prepared in the test method—were added. 4 specimen sheets of 2 cm×2 cm were placed in the solution and shaken at 38° C. for one day. A sample liquid was taken out and one drop (about 0.02 mL) was spread over a Nutrient Broth agar culture ground in an area of about 2×3 cm, and incubated with bacteria, and incubated at 38° C. for one day while monitoring the state of living bacteria. The specimens were again placed in a fresh bacteria solution and the same procedure was repeated 5 times a t maximum.

Test Method—④ (Sundry Bacteria Test)

0.3 gram of dust was taken from a warehouse, added to 100 milliliters of water, dispersed by a homimixer to produce a dispersion, which was filtered with gauze to produce a test bacteria liquid. Evaluation was made in the same manner as in Test method —② except that the bacteria liquid was repeatedly sprayed every week.

The results of the experiments as described above are shown in Tables 4, 5 and 6.

TABLE 4

| | Antibacterial (bactericidal) activity | | | | | |
|---|---|---|---|---|---|---|
| | Test method-① | | Test method-③ | | | |
| Sample | Untreated | 2 days | Times | | | |
| No. | Standard | Washing | 2 | 3 | 4 | 5 |
| 21 | +++ | +++ | +++ | +++ | +++ | +++ |
| 22 | -- | + | ++ | +++ | +++ | +++ |
| 23 | ++ | +++ | +++ | +++ | +++ | +++ |
| 24 | -- | - | - | + | +++ | +++ |
| 25 | + | + | + | +++ | +++ | +++ |
| 26 | + | ++ | ++ | +++ | +++ | +++ |
| 27 | -- | - | -- | - | + | + |
| 28 | - | - | + | + | + | + |
| 29 | + | + | + | ++ | ++ | +++ |
| 30 | -- | - | -- | - | + | + |
| 31 | -- | - | -- | - | + | + |
| 32 | - | + | + | + | ++ | ++ |
| 33 | -- | - | -- | - | + | + |

TABLE 5

| Sample No. | Antifungal activity | | | | |
|---|---|---|---|---|---|
| | Test method-②  | | | Immersion in mud | * |
| | Observations after | | | | |
| | 1 week | 2 weeks | 4 weeks | 4 weeks | 4 weeks |
| 21 | +++ | +++ | +++ | +++ | +++ |
| 22 | -- | - | ++ | +++ | +++ |
| 23 | +++ | +++ | +++ | +++ | +++ |
| 24 | + | ++ | +++ | +++ | +++ |
| 25 | + | ++ | +++ | +++ | +++ |
| 26 | ++ | +++ | +++ | +++ | +++ |
| 27 | - | - | - | + | ++ |
| 28 | + | - | - | + | + |
| 29 | -- | -- | ++ | ++ | ++ |
| 30 | - | - | - | - | - |
| 31 | -- | -- | - | + | + |
| 32 | -- | -- | - | - | - |
| 33 | -- | -- | - | - | - |

* The sheets which were treated 5 times by Test ③ were used.

TABLE 6

| Sample No. | Sundry bacteria resistance activity Test method-④ | | |
|---|---|---|---|
| | Repeated bacteria liquid spray Observations after | | |
| | 1 week | 2 weeks | 4 weeks |
| 21 | +++ | +++ | +++ |
| 22 | + | ++ | +++ |
| 23 | +++ | +++ | +++ |
| 24 | + | +++ | +++ |
| 25 | + | ++ | +++ |
| 26 | +++ | +++ | +++ |
| 27 | - | + | + |
| 28 | + | - | - |
| 29 | - | + | ++ |
| 30 | - | - | - |
| 31 | -- | - | + |
| 32 | -- | - | - |
| 33 | -- | -- | - |

Excellent effects of the present invention could be confirmed from the results shown in Tables 4, 5 and 6. It can be found that the antibacterial antifungal agents of the present invention are greatly superior to benzalkonium chloride of Sample No. 22 which has been known as one of the representative antibacterial antifungal agents.

2-mercaptopyridine-N-oxide of Sample No. 23 has inherently excellent antibacterial and antifungal activities, and however, it is apt to be released from the simply impregnated fibers during washing with water to lose its effects.

Sample Nos. 24, 25 and 26 were those having metal ions simply supported which are Comparative Examples. They have apparently antibacterial antifungal properties, but they are inferior in sustenance and durability.

From the results of Sample Nos. 27 to 33 according to the present invention, the followings are evident:

It could be confirmed that a combination of silver, copper and zinc, and 2-mercaptopyridine-N-oxide is important in keeping both properties of antibacterial and antifungal activities.

The silver ions in this combination acts to improve extremely the antibacterial activity. The copper ions have characteristics of sustaining the effects and of high durability, though they are somewhat lower in the antibacterial activity than that of silver ions. The zinc ions are good at having at least initial antifungal activity without causing any discoloration and contamination of the surfaces of specimens (observations for 1 to 2 weeks in Test method—①).

Sample Nos. 30, 31 and 32 were of a combination of two sorts of metal ions, and Sample No. 33 was of a combination of three of silver, copper and zinc.

The combination of at least two sorts of metal ions gave good results in antibacterial and antifungal activities as well as in sustenance and durability of the activities.

The best results could be obtained in the combination of three.

All the Samples according to the present invention did not show loss of the activities even after irradiation with UV and thermal tests.

EXAMPLE 3

The same procedure as in Example 2 was repeated, except that 1,2-benzisothiazoline-3-one (referred to as BIT hereunder) was used instead of 2-mercaptopyridine-N-oxide.

Similarly to Example 2, there were produced pulps of the followings, from which sheets were made:

CP40AgBIT
CP40CuBIT
CP40ZnBIT
CP40Ag25Cu25Zn50BIT

These sheets exhibited good antibacterial (bactericidal) and antifungal activities identically to those in Example 2.

EXAMPLE 4

The same procedure as in Example 2 was repeated, except that a solution of a mixture of 5-chloro-2-methyl-4-isothiazoline-3-one and 2-methyl-4-isothiazoline-3-one (referred to as MIT hereunder) was used instead of 2-mercaptopyridine-N-oxide. This mix solution had been assayed for its strength by potentiometric titration and adjusted to a concentration of 0.1 M/L before it was used.

Similarly to Example 2, there were produced pulps of the followings, from which sheets were made:

CP40AgMIT
CP40CuMIT
CP40ZnMIT
CP40Ag25Cu25Zn50MIT

These sheets exhibited good antibacterial (bactericidal) and antifungal activities identically to those in Example 2.

EXAMPLE 5

Pulps containing silver, copper and zinc and 2-mercaptopyridine-N-oxide with varying the proportion of the metal ions. The designation was the same as in the previous Examples. Sheets were made similarly to those in Example 2:

Ag5Cu45Zn50MP
Ag10Cu40Zn50MP
Ag20Cu30Zn50MP
Ag40Cu10Zn50MP
Ag20Cu75Zn5MP
Ag20Cu70Zn10MP
Ag20Cu60Zn20MP
Ag20Cu5Zn20MP

In the above systems, silver ions exhibited good antibacterial effects even at a content of 5 mol %. More preferred silver content was in the range of 10 mol % to 30 mol %.

Zinc ions also exhibited sufficient effects at a content of at least 5 mol %. Preferred zinc content could be selected in the range of 5 mol % to 90 mol %.

Copper ion content comprises the remainder of the total amount of metal ions exclusive of silver and copper ions. Copper organic compounds may be limited in its practical use in view of the fact that they may give greenish coloration. Taking account of the fact, The copper content may be selected in the range of about 10 mol % to 75 mol %.

EXAMPLE 6

CP40Ag25Cu25Zn50MP pulp prepared in Example 2 was used and made into sheets identically to Example 2 with varying its formulation to produce the sheets as described below. The basis weight was each 100 g/m$^2$.

The sheets were evaluated for antibacterial activity against colibacillus by Test method ①, antifungal activity against Aspergills riger from observations after 4 we eks by Test method ②, and durability on repeatedly spraying with sundry bacteria liquid by Test method ④. The results are shown in Table 7 with formulations.

TABLE 7

| Sample | Processed pulp content (%) | Test ① | Test ② 4 weeks | Test ④ 4 weeks |
| --- | --- | --- | --- | --- |
| 61 | 0 Comp. Example | +++ | +++ | +++ |
| 62 | 1 Present invention | + | + | + |
| 63 | 3 Present invention | -- | - | - |
| 64 | 10 Present invention | -- | - | - |
| 65 | 20 Present invention | -- | - | - |

It can be appreciated from the results of Table 7 that the pulps filled with antibacterial antifungal agents at high concentrations can provide very high practical effects in a small amount of the pulps to be incorporated.

EXAMPLE 7

Metal complex adsorbed MP pulp was prepared by mixing sequentially the following components:

| | |
| --- | --- |
| Carboxymethylated pulp CP40 (solids content) | 10 grams |
| Water | 500 grams |
| 1N silver nitrate solution pH was adjusted to 5.5 | 2.5 mL |
| 0.1M/L sodium 2-mercaptopyridine-N-oxide solution (0.1M/L MP solution) | 25 mL |
| 1N copper sulfate solution pH was adjusted to 5.5 | 2.5 mL |
| 0.1M/L MP solution | 25 mL |
| 1N zinc nitrate solution pH was adjusted to 5.5 | 5 mL |
| 0.1M/L MP solution | 50 mL |

The pulp was dewatered with a press at pH of 4.

The pulp prepared in this process had good antibacterial antifungal properties identical to those of Sample No. 33.

EXAMPLE 8

Pulps were prepared in the same procedure as Sample No. 33 in Example 2, except that the treatment after the addition of the MP solution was changed as follows:

① Dewatered, washed with water and dewatered at pH=4 in the same manner as in the case of Sample No. 33.
(CP40Ag25Cu25Zn50MP/pH4)

② Dewatered, washed with water and dewatered at pH =5.5.
(CP40Ag25Cu25Zn50MP/pH 5.5)

③ Addition of 15 milliliters of a 1 N copper sulfate solution at pH=5.5, stirred for 30 minutes, dewatered, washed with water and dewatered.
(CP40Ag25Cu25Zn50MP/pH 5.5 Cu)

④ Addition of 15 milliliters of a 1 N zinc nitrate solution at pH=5.5, stirred for 30 minutes, dewatered, washed with water and dewatered.
(CP40Ag25Cu25Zn50MP/pH 5.5 Zn)

Water content yield and percent solids on dryness after press-drying of each of processed pulps are shown in the table below.

| Processed pulps | Water content yield (grams) | Percent solids on dryness (%) |
| --- | --- | --- |
| ① CP40Ag25Cu25Zn50MP/pH 4 | 93 | 12.5 |
| ② CP40Ag25Cu25Zn50MP/pH 5.5 | 128 | 9.3 |
| ③ CP40Ag25Cu25Zn50MP/pH 5.5 Cu | 43 | 28.3 |
| ④ CP40Ag25Cu25Zn50MP/pH 5.5 Zn | 51 | 23.9 |

It can be seen that the copper and zinc ions added in the post-treatment acted to cause a great reduction in swelling of processed pulps.

Sheets were made in the same procedure as described in the term "Production of water resistant sheets" of Example 2, except that 40 parts by weight of polyester fibers, 40 parts by weight of binder fibers and 20 parts by weight of each of the above pulps ① to ④ were used.

Pulps ③ and ④ exhibited less breakdown during beating, good freeness, good releasability from filter paper, and rapid drying. Each sheet had good antibacterial (bactericidal) and antifungal effects.

Each sheet was placed in a sealed vessel containing ammonia gas or hydrogen sulfide. The pulp ③ was discolored to blue-green color in ammonia gas. All the sheets were discolored to blackish brown with most significant discoloration of the sheet ③. The sheets had antibacterial antifungal activities, deodorizing property (gas absorbing property), and discoloration displaying property (indicator).

EXAMPLE II

The filter materials containing the fibrous materials which contain the antibacterial antifungal agents according to the present invention will be practically explained with reference to Examples, without being limited thereto.

"Parts" and "%" in the following Examples are based by weight.

Example A

In the similar procedure to that described in the previous embodiment of the present invention, fibrous materials containing an antibacterial antifungal agent which comprised a metal salt of organic compound consisting of a modified NBKP of a degree of substitution with carboxymethyl group of 0.22 (DS=0.22) having Ag/2-mercaptopyridine-N-oxide adsorbed were prepared (referred to as CP22AgMP by abbreviation). Silver nitrate was added to the aforementioned modified NBKP dispersion which was adjusted to pH 5.5, and stirred for 30 minutes. 0.1 M/L sodium 2-mercaptopyridine-N-oxide solution was added to the NBKP dispersion in an equimolar amount as the amount of silver nitrtate added. After stirring for 30 minutes, the pH was lowered to 4 with sulfuric acid, and the product was dewatered.

Again 500 milliliters of water were added to the dewatered pulp, stirred, washed with water, and then dewatered.

This is referred to as modified NBKP of a degree carboxymethlation of 0.22 (DS=0.22) containing an antibacterial antifungal agent which comprises a metal salt of organic compound having Ag/2-mercaptopyridine-N-oxide adsorbed.

Comparative Example 1

To a 2 m$^3$ dispersion tank were added a sodium acrylate anionic surfactant (available from Nippon Acryl Chemical Co. under the tradename, Primal 850) in an amount of 1% on the basis of the total of fibers, polypropylene fibers (a diameter of about 7 μm) (PZ 0.5 denier, 5 mm, the product of Daiwa Boseki), MBF-E composite fibers (core: polypropylenes, sheath: ethylenevinylalcohol, the product of Daiwa Boseki) and vinylone binder fibers having a dissolving temperature in water of 70° C. (VPB 107×1.3 mm; the product of Kuraray Co.) in a ratio of 50:44:6 to produce a dispersion having a dispersion concentration of 0.2%, which was stirred for 30 minutes, made into sheets by a cylinder paper machine to a dry weight of 70 grams/M$^2$, and dried with a cylindrical drier at its surface temperature of 130° C. to produce filter materials.

Examples 1 to 5

Filter materials for Examples 1 to 5 were prepared in the same procedure as in Comparative Example 1, except that a part of the polypropylene fibers of Comparative Example 1 was replaced by the fibrous materials, CP22AgMP obtained in Example A as above according to the present invention in the amount incorporated as indicated in Table 1.

Example B

In the similar procedure to that in Example A and in accordance with the previous embodiment of the present invention, fibrous materials containing an antibacterial antifungal agent which comprised a metal salt of organic compound consisting of a modified NBKP of a degree of substitution with carboxymethyl group of 0.40 (DS=0.40) having Cu/1,2-benzisothiazoline-3-one adsorbed were prepared (referred to as CP40CuBIT by abbreviation) instead of CP22AgMP.

Comparative Example 2

To a 2 m$^3$ dispersion tank were added a sodium acrylate anionic surfactant (available from Nippon acryl chemical Co. under the tradename, Primal 850) in an amount of 1% on the basis of the total of fibers, acrylic fibers of a diameter of 0.1 denier×3 mm, fibrillated organic fibers (KY-400S: the product of Daicel Chemical Industry Co.), polyester fibers of a diameter of 0.5 denier×5 mm (available from Teijin Co.), and polyester binder fibers having a diameter of 2 denier×5 mm (Melty 4080, the product of Unitika Co.) in a ratio of 50:5:20 : 25 to produce a dispersion having a dispersion concentration of 0.2%, which was stirred for 30 minutes, made into sheets of a dry weight of 80 grams/m$^2$ by a cylinder paper machine, dried with a cylindrical drier at its surface temperature of 130° C., sized with a water repellant and acrylic latex by a sizing press system, and dried to produce filter materials.

Examples 6 to 10

Filter materials for Examples 6 to 10 were prepared in the same procedure as in Comparative Example 2, except that a part of the acrylic fibers of Comparative Example 2 was replaced by the fibrous materials, CP40CuBIT obtained in Example B as above according to the present invention in the amount incorporated as indicated in Table 1.

Example C

In the similar procedure to that in Example A and in accordance with the previous embodiment of the present invention, fibrous materials containing an antibacterial antifungal agent which comprised a metal salt of organic compound consisting of a modified NBKP of a degree of substitution with carboxymethyl group of 0.40 (DS=0.40) having (Ag, Cu, Zn)/2-mercaptopyridine-N-oxide adsorbed were prepared (referred to as CP40Ag25Cu25Zn50MP by abbreviation) instead of CP22AgMP.

The number after each metal atom represents mol% ratio of the metal atom.

Comparative Example 3

To a 2 m$^3$ dispersion tank were added a sodium acrylate anionic surfactant (mfd. by Nippon Acryl Chemical Co. under the trade name, Primal 850) in an amount of 1% on the basis of the total of fibers, polyester fibers (a diameter of about 7 μm)(0.5 denier, 5 mm: the product of Teijin Co.), and polyester binder fibers having a diameter of 2 denier×5 mm (Melty 4080, the product of Unitika Co.), and microglass fibers of an average diameter of about 0.65 μm (# 106, the product of Shuler Co.) in a ratio of 50:35:15 to produce a dispersion having a dispersion concentration of 0.2%, which was stirred for 30 minutes, made into sheets of a dry weight of 100 grams/m$^2$ by a cylinder paper machine, dried with a cylindrical drier at its surface temperature of 130° C. to produce filter materials.

Examples 11 to 15

Filter materials for Examples 11 to 15 were prepared in the same procedure as in Comparative Example 3, except that a part of the polyester fibers of a diameter of 0.5 denier of Comparative Example 3 was replaced by the fibrous materials, CP40Ag25Cu25Zn50MP obtained in Example C as above according to the present invention in the amount incorporated as indicated in Table 1.

Example 16

Filter materials for Example 16 were prepared in the same procedure as in Example 13, except that the polyester fibers of a diameter of 0.5 denier were replaced by 20 parts by weight of activated carbon fibers (an average diameter of 15 μm, a length of 8 mm, a specific surface area of 1000 m$^2$/gram).

Comparative Example 4

Filter materials for Comparative Example 4 were prepared in the same procedure as in Example 16, except that the fibrous materials of the present invention, CP40Ag25Cu25Zn50MP were not employed.

Comparative Example 5

Filter materials for Comparative Example 5 were prepared in the same procedure as in Example 13, except that 10% of fibrous materials containing benzalkonium chloride were used instead of the fibrous materials containing CP40Ag25Cu25Zn50MP with a combination of three metal salts of the present invention.

The fibrous materials containing benzalkonium chloride were prepared by adding 100 millimeters of a 0.1 M/L benzalkonium chloride solution based on 10 grams of modified NBKP having a degree of substitution with carboxymethyl group of 0.40 (DS=0.40) which was used in Example 13, adjusting its pH to 5.5, stirring, dewatering, washing with water and then again dewatering.

Example 17

A pulp slurry consisting of 70 parts by weight of activated carbon fibers, 20 parts by weight of NBKP (Canadian Standard freeness: 550 mL) and 10 parts by weight of MBF-E composite fibers (core: polypropylene, sheath: polyethylene vinylalcohol, the product of Daiwa Boseki) and a pulp slurry from Example 13 were simultaneously made into sheets by a cylinder paper-machine and a Fourdrinier paper machine to a dry weight of 200 grams/m$^2$ (100 grams/m$^2$ for each), both sheets of which were placed on top of the other and dried with a cylindrical dryer at its surface temperature of 130° C. to produce filter materials.

Example 18

In Example 18, the filter materials from Example 14 were subjected to skirt folding process and incorporated in a unit which was set in a circulating system inside an automobile room.

Comparative Example 6

In Comparative Example 6, the filter materials from Comparative Example 3 were subjected to skirt folding process and incorporated in a unit which was set in a circulating system inside an automobile room.

The thus produced filter materials from Examples and Comparative Examples were evaluated for loss of pressure, capturing efficiency, antibacterial activity, and antifungal activity. The results obtained are shown in Table 9.

Loss Of Pressure

Loss of pressure (Pa) was determined by measuring an air pressure drop through the filter, when passing an air flow through the filter at a velocity of 5.3 cm/sec.

Capturing Efficiency

Capturing efficiency (%) was determined by producing DOP airosol particles (dioctyl phthalate, a particle size of 0.3 4m), which were entrained in an air flow, and passing the air flow through the filter at a velocity of 5.3 cm/sec. and sampling the air before and after the filter, the particle concentration of which were measured with a multi-dust counter, and calculating using the following formula:

Capturing efficiency ={ (Number of particles before filter−Number of particles after filter)/Number of particles before filter} ×100

Test—①  (Antibacterial (Bactericidal) Activity)

The same test procedure as "Test—②  (antibacterial (bactericidal) activity)" was employed.

Test—②  (Antifungal Activity)

The same test procedure as "Test—②  (antifungal activity)" was employed. Table 9 represents the results of observations after 4 weeks elapsed.

TABLE 9

| Example | Incorporation % | Capturing efficiency | Loss of pressure | Antibacterial Act. | Antifungal Act. |
|---|---|---|---|---|---|
| 1 | 3 | 23.5 | 9.8 | + | + |
| 2 | 5 | 23.5 | 9.9 | − | − |
| 3 | 10 | 23.3 | 9.7 | −− | −− |
| 4 | 15 | 23.0 | 9.5 | −− | −− |
| 5 | 30 | 22.8 | 9.4 | −− | −− |
| Comp. Ex. 1 | 0 | 23.5 | 9.8 | +++ | +++ |
| 6 | 3 | 63.5 | 37.2 | + | + |
| 7 | 5 | 63.2 | 37.0 | − | − |
| 8 | 10 | 63.0 | 36.5 | −− | −− |
| 9 | 15 | 62.9 | 36.2 | −− | −− |
| 10 | 30 | 62.5 | 35.4 | −− | −− |
| Comp. Ex. 2 | 0 | 63.5 | 37.2 | +++ | +++ |
| 11 | 3 | 75.6 | 48.8 | − | − |
| 12 | 5 | 75.2 | 48.5 | − | −− |
| 13 | 10 | 75.0 | 47.9 | −− | −− |
| 14 | 15 | 74.5 | 47.3 | −− | −− |
| 15 | 30 | 73.8 | 46.5 | −− | −− |
| Comp. Ex. 3 | 0 | 75.8 | 49.0 | +++ | +++ |
| 16 | 10 | 73.8 | 46.0 | −− | −− |
| Comp. Ex. 4 | 0 | 74.0 | 46.6 | +++ | ++ |
| Comp. Ex. 5 | 10* | 75.1 | 48.0 | ++ | ++ |
| 17 | 10 | 85.8 | 73.5 | −− | −− |

Note)
10* of Comparative Example 5 represents the use of 10% of the fibrous materials containing benzalkonium chloride instead of the fibrous materials containing the three metal salt system CP40Ag25Cu25Zn50MP of the present invention.

The results shown in Table 9 indicate the followings:

The filter materials, one of the fibers constructing which, i.e., the polypropylene fibers were partly replaced by the fibrous materials containing the antibacterial antifungal agent (CP22AgMP) described in Example A of the present invention, were found to have superior antibacterial and antifungal activities to those of the Comparative Example 1 which did not contain the antibacterial antifungal agent. The effects could be observed in the amount of the agent incorporated in the range of 3% or more. Considerably good antibacterial antifungal effects could be observed in the range of 5% or more with extremely good antibacterial antifungal effects being observed at 10% or more.

The capturing efficiency was observed to have a tendency to somewhat decline as compared with Comparative Example 1 in the incorporated amount of 30% or more. However, the produced filter materials had no practical objection.

The filter materials of Examples 6 to 10, where one of the fibers constructing the filter materials, i.e., the acrylic fibers were partly replaced by the fibrous materials containing the antibacterial antifungal agent (CP22CuBIT) described in Example B of the present invention, were found to have good antibacterial and antifungal activities identically to those of Examples 1 to 5.

The filter materials having glass fibers incorporated of Examples 11 to 15, where one of the fibers constructing the filter materials, i.e., the polyester fibers of 0.5 denier were partly replaced by the fibrous materials containing the antibacterial antifungal agent (CP40Ag25Cu25Zn50MP) described in Example C of the present invention, were found to have good filter properties as well as extremely good antibacterial and antifungal activities due to the effects of the combination of three metal salts identically to those of Examples 6 to 10.

The filter materials of Example 16, where the polyester fibers of 0.5 denier of Example 13 were partly replaced by the activated carbon fibers and the antibacterial antifungal agent with the combination of three metal salts was used, were found to have good filter properties and extremely good antibacterial and antifungal activities. It was also noted that they had deodorant effects.

The filter materials of Example 17, where the activated carbon fibers and other fibers of Example 13 were simultaneously made into sheets and both sheets were laminated, had extremely good antibacterial and antifungal activities as well as excellent deodorant effects. Moreover, they exhibited outstanding effects on the test by Test—③ (sundry bacteria test).

Therefore, the fibrous materials of the present invention have optimum utility as air filters for automobiles.

Comparative Example 5

The filter materials in this Comparative Example were the same as those in Example 13, except that 10% of the fibrous materials containing benzalkonium chloride were used instead of the fibrous materials containing the antibacterial antifungal agent of the three metal salt system, CP40Ag25Cu25Zn50MP of the present invention. They were found to have initial antibacterial and antifungal effects, but they were very inferior in the long term (4 weeks) effects to those of Example 13.

In Example 18

In Example 18, the filter materials from Example 14 were subjected to skirt folding process and incorporated in a unit which was set in a circulating system inside an automobile room. There was no mold odor in the air blown out at the outlet.

Comparative Example 6

In Comparative Example 6, the filter materials from Comparative Example 3 were subjected to skirt folding process and incorporated in a unit which was set in a circulating system inside an automobile room. There was mold odor in the same test as in Example 18.

Example 19

The wall materials containing the fibrous materials which contain the antibacterial antifungal agents of metal salts of organic compounds according to the present invention could suppress the generation of mold for quite a long period of time as compared to those not containing the fibrous materials.

Example 20

The insole materials containing the fibrous materials which contain the antibacterial antifungal agents of metal salts of organic compounds according to the present invention could suppress the generation of mold and also well suppress the generation of malodor as compared to those not containing the fibrous materials.

As described above in detail, the fibrous materials containing the antibacterial antifungal agents according to the present invention utilize skillfully the unique porosity of the fibrous materials to form hydrophilic matrix. Therefore, they have a good bacteria-capturing property, high moisture retaining function, and good ion-dispersing property for various ions. Moreover, the antibacterial antifungal agents of the present invention are less soluble and appropriately dissociative so that they exhibit sustained release. Therefore, they are capable of sustaining the antibacterial antifungal effects to have a long life and excellent durability.

The most effectively functional fibrous materials containing the antibacterial antifungal agents according to the present invention are obtained when fibrous materials used are partly modified cellulose fibers which are modified by carboxmethylation and have a degree of substitution (DS) of 0.5 or less. The use of pulps consisting of such fibrous materials allows production of pulps having an extremely high content of antibacterial antifungal agents because the agents can be filled at a high concentration in the cellulose fibers constituting the pulps.

Moreover, the fibrous materials containing the antibacterial antifungal agents according to the present invention can be formed even into sheet-like articles at high throughput. The pulps as above can be applied to a part of a sheet-like article, for example, stock of paper or various fabrics to exhibit sufficient effects, even when they are speckle-distributed in the sheet-like article due to the high concentration of the antibacterial antifungal agents filled. Consequently the objects can be achieved by the use of small amounts of the fibrous materials. Therefore, despite the high antibacterial antifungal effects, sheet-like articles having relatively high safety can be obtained.

Therefore, various articles containing the fibrous materials which contain the antibacterial antifungal agents according to the present invention can be used, for example, in various filter materials, especially various air filters, above all preferably those for automobiles. The fibrous materials containing the antibacterial antifungal agents according to the present invention have been found to exhibit high antibacterial antifungal effects when they are applied to walls and insoles.

What is claimed is:

1. A fibrous material containing an antibacterial antifungal agent comprising a metal salt of an organic compound wherein said metal salt is a complex of a silver salt, a copper salt and a zinc salt.

2. The fibrous material according to claim 1, wherein said complex of three of a silver salt, a copper salt and a zinc salt has a composition of 10 to 40 silver, 20 to 60 zinc and the remainder copper by mole based on 100 moles of the total of metals, provided that the amount of copper is never zero.

3. The fibrous material according to claim 1, wherein said organic compound is a compound containing at least one of sulfur atoms and heterocyclic rings with hetero-nitrogen atom.

4. The fibers material according to claim 3, wherein said organic compound containing at least one of sulfur atoms and heterocyclic rings with hetero-nitrogen atom is at least one selected from the group consisting of benzimidazole compounds, mercaptopyridine-N-oxide compounds, isothiazolone compounds, benzothiazole compounds and benzothiazolone compounds.

5. A fibrous material containing an antibacterial antifungal agent comprising a metal salt of an organic compound, wherein said fibrous material is ion-exchange fibers and said ion-exchange fibers are carboxymethyl-modified cellulose fibers by substitution on said cellulose with carboxymethyl group.

6. The fibrous material according to claim 5, wherein said carboxymethyl group substitution on said cellulose has a degree of substitution of 0.5 or less, as measured bv the degree of carboxymethyl group substitution per glucose unit.

7. The fibrous material according to claim 5, wherein a proportion of said antibacterial antifungal agent is 1% or more solids by weight based on said carboxymethyl-modified cellulose fibers.

8. A fibrous material containing an antibacterial antifungal agent produced by:
   adding a metal salt to ion-exchange fibers selected from the group consisting of polystyrenes, polyacrylics, polyamides, polyesters, polyethylenes and cellulose, said ion-exchange fibers having an acid group selected from the group consisting of sulfonic acid group, phosphonic acid group and carboxylic acid group; and then adding an organic compound, wherein said metal salt is a complex of a silver slat, a copper salt and a zinc salt.

9. The fibrous material containing an antibacterial antifungal agent according to claim 8, wherein said organic compound is a compound containing at least one of sulfur atoms and heterocyclic rings with hetero-nitrogen atom.

10. The fibrous material containing an antibacterial antifungal agent according to claim 9, wherein said organic compound containing at least one of sulfur atoms and heterocyclic rings with hetero-nitrogen atom is at least one selected from the group consisting of benzimidazole compounds, mercaptopyridine-N-oxide compounds, isothiazolone compounds, benzothiazole compounds and benzothiazolone compounds.

11. A fibrous material containing an antibacterial antifungal agent produced by:

adding a metal salt to ion-exchange fibers selected from the group consisting of polystyrenes, polyacrylics, polyamides, polyesters, polyethylenes and cellulose, said ion-exchange fibers having an acid group selected from the group consisting of sulfonic acid group, phosphonic acid group and carboxylic acid group; and then adding an organic compound, wherein said ion-exchange fibers are carboxymethyl-modified fibers by substitution on said at least one polyacrylics, polyamides, polyesters, polyethylenes and cellulose, with carboxymethyl group.

12. The fibrous material containing an antibacterial antifungal agent according to claim 11, wherein said ion-exchange fibers are carboxymethyl-modified cellulose fibers by substitution on said cellulose with carboxymethyl group.

13. The fibrous material according to claim 12, wherein said carboxymethyl group substitution on said cellulose has a degree of substitution of 0.5 or less, as measured by the degree of carboxymethyl group substitution per glucose unit.

14. A fibrous material containing an antibacterial antifungal agent produced by:

adding a metal salt to ion-exchange fibers selected from the group consisting of polystyrenes, polyacrylics, polyamides, polyesters, polyethylenes and cellulose, said ion-exchange fibers having an acid group selected from the group consisting of sulfonic acid group, phosphonic acid group and carboxylic acid group; and then adding an organic compound, wherein said fibrous material is produced by adding at least one selected from the group consisting of silver salts, copper salts and zinc salts to a carboxymethyl modified cellulose being substituted with carboxymethyl group, followed by adding at least one selected from the group consisting of benzimidazole compounds, mercaptopyridine-N-oxide compounds, isothiazolone compounds, benzothiazole compounds and benzothiazolone compounds at a pH of 5 to 8.

15. The fibers material containing an antibacterial antifungal agent according to claim 14, wherein said fibrous material is produced by adding two or more selected from a silver salt, a copper salt and a zinc salt to a carboxymethyl modified cellulose being substituted with carboxymethyl group, followed by adding at least one selected from the group consisting of benzimidazole compounds, mercaptopyridine-N-oxide compounds, isothiazolone compounds, benzothiazole compounds and benzothiazolone compounds at a pH of 5 to 8.

16. The fibers material containing an antibacterial antifungal agent according to claim 15, wherein said fibrous material is produced by adding three metal salts of a silver salt, a copper salt and a zinc salt to a carboxymethyl modified cellulose being substituted with carboxymethyl group, followed by adding at least one selected from the group consisting of benzimidazole compounds, mercaptopyridine-N-oxide compounds, isothiazolone compounds, benzothiazole compounds and benzothiazolone compounds at a pH of 5 to 8.

17. The fibers material containing an antibacterial antifungal agent according to claim 16, wherein said fibrous material is produced by adding three metal salts of a silver salt, a copper salt and a zinc salt to a carboxymethyl modified cellulose being substituted with carboxymethyl group, followed by adding a mercaptopyridine-N-oxide compound at a pH of 5 to 8.

18. The fibers material containing an antibacterial antifungal agent according to claim 17, wherein said fibrous material is produced by adding a silver salt to a carboxymethyl modified cellulose being substituted with carboxymethyl group, then adding a mercaptopyridine-N-oxide compound to the resulting mixture at a pH of 5 to 8, followed by adding a copper salt, and then adding a mercaptopyridine-N-oxide compounds the resulting mixture at a pH of 5 to 8 followed by adding a zinc salt, and then adding a mercaptopyridine-N-oxide compound to the resulting mixture at a pH of 5 to 8.

19. The fibers material containing an antibacterial antifungal agent according to claim 16, wherein said fibrous material is produced by adding at least two of a silver salt, a copper salt and a zinc salt to a carboxymethyl modified cellulose being substituted with carboxymethyl group, and then adding at least one compound selected from benzimidazole compounds, mercaptopyridine-N-oxide compounds, isothiazolone compounds, benzathiazole compounds and benzothiazolone compounds at a pH of 5 to 8, followed by adding a zinc salt.

20. The fibers material containing an antibacterial antifungal agent according to claim 19, wherein said fibrous material is produced by adding at least two of a silver salt, a copper salt and a zinc salt to a carboxymethyl modified cellulose being substituted with carboxymethyl group, then adding a mercaptopyridine-N-oxide compound at a pH of 5 to 8, followed by adding a zinc salt.

21. The fibers material containing an antibacterial antifungal agent according to claim 16, wherein said fibrous material is produced by adding at least two of a silver salt, a copper salt and a zinc salt to a carboxymethyl modified cellulose being substituted with carboxymethyl group, and then adding at least one compound selected from benzimidazole compounds, mercaptopyridine-N-oxide compounds, isothiazolone compounds, benzothiazole compounds and benzothiazolone compounds at a pH of 5 to 8, followed by adding a copper salt.

22. The fibers material containing an antibacterial antifungal agent according to claim 21, wherein said fibrous material is produced by adding at least two of a silver salt, a copper salt and a zinc salt to a carboxymethyl modified cellulose being substituted with carboxymethyl group, then adding a mercaptopyridine-N-oxide compound at a pH of 5 to 8, followed by adding a copper salt.

* * * * *